United States Patent [19]

Meienhofer

[11] 4,426,324

[45] Jan. 17, 1984

[54] IMMUNOPOTENTIATING PEPTIDES

[75] Inventor: Johannes A. Meienhofer, Upper Montclair, N.J.

[73] Assignee: Hoffmann-La Roche Inc., Nutley, N.J.

[21] Appl. No.: 144,516

[22] Filed: Apr. 28, 1980

Related U.S. Application Data

[63] Continuation-in-part of Ser. No. 79,630, Sep. 28, 1979, abandoned.

[51] Int. Cl.$^3$ ............................................ C07C 103/52
[52] U.S. Cl. ............................................ 260/112.5 R
[58] Field of Search ................................ 260/112.5 R

[56] References Cited

U.S. PATENT DOCUMENTS 4,148,788  4/1979  Wang ......................... 260/112.5 R

OTHER PUBLICATIONS

Pettit, Synthetic Peptides (1971) pp. 106–107.
Akiko, et al., Chem. Pharm. Bull. 27, 3171–3175 (1979).
Birr, et al., Angew. Chem. Int. Ed. Engl. 18, (1979) 394–395.

Primary Examiner—Delbert R. Phillips
Attorney, Agent, or Firm—Jon S. Saxe; Bernard S. Leon; George M. Gould

[57] ABSTRACT

Novel di-to heptapeptides representing fragments of the carboxyl terminal of thymosin $\alpha_1$ are active as agents which affect regulation, differentiation and function of thymus dependent lymphocytes.

6 Claims, No Drawings

IMMUNOPOTENTIATING PEPTIDES

RELATED APPLICATION

This application is a continuation-in-part of copending U.S. Ser. No. 79,630, filed Sept. 28, 1979, now abandoned.

BACKGROUND OF THE INVENTION

Several polypeptide factors present in the thymus gland have been implicated to play important roles in the development and maintenance of immunological competence in man and in animals. The importance of the immune system in the defense against cancer and tumor cells is now widely recognized. In recent years, a few polypeptides shown to be able to stimulate maturation, differention and function of T cells have been isolated from bovine thymus. Among them, the peptide thymosin $\alpha_1$ has been intensively studied. Its structure and activity have been described in U.S. Pat. No. 4,079,127.

Additionally, in the course of synthesizing thymosin $\alpha_1$ by solution phase methodology, Wang in U.S. Pat. No. 4,148,788 utilized the protected carboxyl terminal octa-, undeca- and tetradecapeptides of thymosin $\alpha_1$ as intermediates. These compounds were also deprotected by hydrogenolysis followed by treatment with HF and the resulting free peptides were indicated to have activity in the regulation, differentiation and function of T-cells.

In addition, this patent described the preparation and use as intermediates in the synthesis of thymosin $\alpha_1$ of the protected carboxyl terminal tripeptide Ala—Glu(OBzl)—Asn—OBzl and the protected carboxyl terminal pentapeptide H—Glu(OBzl)—Glu(OBzl)—Ala—Glu(OBzl)—Asn—OBzl. No teaching or suggestion appears in this patent to deprotect either of these compounds nor is there any suggestion that the resulting free peptides might exhibit immunostimulatory activity.

The carboxyl terminal tetrapeptide in protected form, i.e., H—Glu(OBu$^t$)—Ala-Glu(OBu$^t$)—Asn(MbH)OBzl where Bu$^t$=tert. butyl and MbH=4,4'dimethoxybenzhydryl has been described by Birr and Stollenwerk, in Angew. Chem., 91, 422 (1979) as an intermediate in the synthesis of thymosin $\alpha_1$ by an alternate scheme from that suggested by Wang, supra. However, there is no teaching or suggestion in this paper that such compound be deprotected to the free peptide or that such free peptide, if prepared, would exhibit immunostimulatory activity.

DESCRIPTION OF THE INVENTION

The present invention relates to novel peptides related to the di- through heptapeptide sequence of the carboxyl terminal of the known immunostimulatory thymic peptide thymosin $\alpha_1$. Such peptides can be conveniently represented by the following formula:

X—Glu—Asn—OH      I where X is H, H—Ala—, H—Glu—Ala—, H—Glu—Glu—Ala—, H—Val—Glu—Glu—Ala— or H—Val—Val—Glu—Glu—Ala— and the pharmaceutically acceptable salts thereof.

Particularly preferred compounds of formula I include the tripeptide H—Ala—Glu—Asn—OH and the pentapeptide H—Glu—Glu—Ala—Glu—Asn—OH.

The compounds of the present invention can be readily prepared by removal of protective groups from corresponding protected peptides, either known or novel, using procedures well known in the art for removal of such protecting groups. Thus, for example, the compounds of formula I of the present invention can be readily prepared from the corresponding protected compounds of the formula

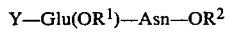

where Y is A—, A—Ala—, A—Glu(OR$^1$)—Ala—, A—Glu(OR$^1$)—Glu(OR$^1$)—Ala—, A—Val—Glu(OR$^1$)—Glu(OR$^1$)—Ala—, or A—Val—Val—Glu(OR$^1$)—Glu(OR$^1$)—Ala—, where A is a conventional α-amino protecting group preferably t-butyloxycarbonyl (Boc) or benzyloxycarbonyl (Z); and R$^1$ is a conventional protecting group for carboxyl groups selected from esters such as aryl esters, particularly phenyl or phenyl substituted with lower alkyl, halo, nitro, thio or substituted thio, i.e., lower alkyl thio, preferably methyl thio, aralkyl esters such as benzyl or benzyl substituted with methoxy, halo or nitro, lower alkyl esters such as methyl, ethyl, tert-butyl and tert-amyl, substituted lower alkyl esters such as 2-haloethyl, β,β-dimethyl-aminoethyl and cyanomethyl, benzhydryl esters and phenacyl esters; and R$^2$ is selected from the carboxyl protecting groups set forth in R$^1$ above by removal of the protecting groups in a manner known per se such as, for example, by treatment with anhydrous hydrofluoric acid (HF) preferably in the presence of anisole.

Compounds of formula II not already known in the art may be readily synthesized in analogy to known procedures. Thus, for example, the hexapeptide A—Val—Glu(OR$^1$)—Glu—(OR$^1$)—Ala—Glu(OR$^1$)—Asn—OR$^2$ (III) can be obtained by the reaction of A—Val—OH and HCl.Glu(OR$^1$)—Glu(OR$^1$)—Ala—Glu(OR$^1$)—AsnOR$^2$ (V) using dicyclohexyl-carbodiimide (DCC) and N-hydroxysuccinimide (HOSU). The aforesaid pentapeptide V is obtained from the corresponding known Boc protected compound by a 30 minute treatment with 4 N HCl in dry tetrahydrofuran.

In similar fashion, the heptapeptide A—Val—Val—Glu(OR$^1$)—Glu(OR$^1$)—Ala—Glu(OR$^1$)—AsnOR$^2$ can be obtained by the reaction of A—Val—Val—OH and pentapeptide V using DCC and HOSU as before.

In a further aspect of the present invention the di- to heptapeptide of formula I were prepared by solid phase peptide synthesis. In such embodiment commerically available benzhydrylamine resin was neutralized and acylated with N α-Boc-α-benzyl-L-aspartic acid in the presence of DCC to give Boc-asparaginyl resin. This amino acid resin was then benzoylated according to the procedure of Wang, J. Amer. Chem. Soc. 95, 1328 (1973) and placed into the reaction vessel of an automated peptide synthesis apparatus. The machine was then programmed to perform the solid phase synthesis to incorporate the following amino acid unit in each cycle sequentially:

| | |
|---|---|
| Boc—Glu(OBzl)—OH | (stop synthesis for dipeptide) |
| Boc—Ala—OH | (stop synthesis for tripeptide) |
| Boc—Glu(OBzl)—OH | (stop synthesis for tetrapeptide) |
| Boc—Glu(OBzl)—OH | (stop synthesis for pentapeptide) |

| | |
|---|---|
| Boc—Val—OH | (stop synthesis for hexapeptide) |
| Boc—Val—OH | (stop synthesis for heptapeptide). |

Four fold excess of each Boc-amino acid and DCC were used in each coupling reaction (120 minutes) and a 30 minute treatment with 33% trifluoroacetic acid in methylene chloride was used as deprotecting agent for the Boc-group. The respective protected peptide resins of the formula

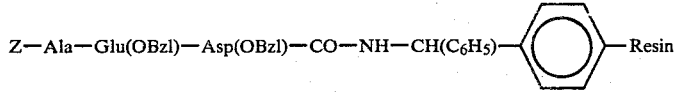

where Z is Boc—, Boc—Glu(OBzl); Boc—Glu(OBzl)—Glu(OBzl)—, Boc—Val—Glu(OBzl)—Glu(OBzl)— or Boc—Val—Val—Glu(OBzl)—Glu(OBzl)-VI thus obtained were then treated with anhydrous HF-anisole to remove all the side chain protecting groups and at the same time to release the unprotected peptide from the resin. The crude peptides were desalted on a Sephadex G-10 column and then purified by column chromatography, i.e., DEAE-Sephadex A-25. While specific protecting groups have been disclosed in regard to the solid phase synthesis aspect, it should be noted that each amino acid can be protected by any of the protective groups described for the respective amino acids in solution phase synthesis.

In an alternative embodiment for preparing the compounds of the present invention by solution phase syntheses, a scheme is employed utilizing the benzyloxycarbonyl group for α-amino group protection and the tert-butyl group for side chain carboxyl group protection.

The dipeptide was conveniently prepared from Z—Glu(OtBu)—Asn—OtBu by removing the α-amino protecting group by catalytic hydrogenation over a suggested palladium catalyst, e.g. 5% Pd-BaSO4 followed by removal of the side-chain protecting groups of the resulting H—Glu(OtBu)—Asn—OtBu by treatment with a solution of 1:1 (v/v) of trifluoroacetic acid (TFA)-methylene chloride ($CH_2Cl_2$) to yield the desired H—Glu—Asn—OH.

Conversion of H—Glu(OtBu)—Asn—OtBu to the tripeptide of the invention was accomplished by reaction with Z—Ala—OH utilizing the mixed anhydride method (isobutylchloroformate-N-methylmorphine), followed by deprotection of the resulting Z—Ala—Glu(OtBu)—Asn—OtBu by catalytic hydrogenation (5% Pd-BaSO4) to yield H—Ala—Glu(OtBu)—Asn—OtBu and then treatment with 1:1 TFA-$CH_2Cl_2$ to give the desired H—Ala—Glu—Asn—OH.

Reaction of H—Ala—Glu(OtBu)—Asn—OtBu with Z—Glu(OtBu)—OH by the mixed anhydride method and stepwise deprotection of the resulting Z—Glu(OtBu)—Ala—Glu(OtBu)—Asn—OtBu in analogous fashion to the above-described procedures yields the desired tetrapeptide—H—Glu—Ala—Glu—Asn—OH.

Syntheses of the hexapeptide is accomplished by condensation of the tetrapeptide intermediate H—Glu(OtBu)—Ala—Glu(OtBu)—Asn—OtBu with Z—Val—Glu(OtBu)—NHNH2 utilizing conventional azide coupling conditions (isoamylnitrite/HCl) providing Z—Val—Glu(OtBu)—Glu(OtBu)—Ala—Glu(OtBu)—Asn—OtBu which is deprotected in stepwise fashion as above to yeild the desired H—Val—Glu—Glu—Ala—Glu—Asn—OH.

Preparation of the heptapeptide of the invention may be carried out by condensing the fragments Z—Val—Val—Glu(OtBu)—NHNH2 with H—Glu(OtBu)—Ala—Glu(OtBu)—Asn—OtBu under conventional azide coupling conditions to yield Z—Val—Val—Glu(OtBu)—Glu(OtBu)—Ala—Glu(OtBu)—Asn—OtBu which is deprotected in stepwise fashion as above to obtain H—Val—Val—Glu—Glu—Ala—Glu—Asn—OH.

The compounds of formula I of the present invention have activity in the regulation, differentiation and function of T-cells. Such activity must be considered unexpected in view of the knowledge in the peptide hormone art that the deletion of even one amino acid from the sequence of a biologically active peptide can result in the loss of biological activity. This is particularly true for relatively small peptide molecules.

The instant compounds may be administered to warm blooded mammals by parenteral application either intravenously, subcutaneously or intramuscularly. These compounds are potent immunopotentiating agents with a daily dosage in the range of about 0.1 to 50 mg/kg of body weight per day for intravenous administration. Obviously, the required dosage will vary with the particular condition being treated, the severity of the condition and the duration of treatment. A suitable dosage form for pharmaceutical use is 1 to 5 mg of lyophilized compound of formula I to be reconstituted prior to use by the addition of sterile water or saline.

Also indicated within the scope of the present invention are the pharmaceutically acceptable salts of the compounds of formula I. Suitable salts include sodium, potassium or a strong organic base such as guanidine. In addition, the counter ions of these cations such as the chloride, bromide, sulfate, phosphate, malate, ascorbate and the like, may be included in the preparation.

The present invention is further illustrated by the Examples which follow.

EXAMPLE 1

H—Ala—Glu—Asn—OH

The protected tripeptide HCl—Ala—Glu(OBzl)—Asn—OBzl (220 mg., 0.4 mM) was dissolved in methanol (15 ml) containing acetic acid (02. ml) and hydrogenated in the presence of 10% Pd/C (220 mg) for 3 hrs. at atm. and room temperature. The catalyst was removed by filtration and the filtrate concentrated and lyophilized.

Yield; 110 mg (74.7%)

Amino Acid Analysis: Asp, 1.00; Ala, 1.04; Glu, 0.95.

The product was homogeneous on TLC:

$R_f$ 0.47 (n-propanol:water; 7:3) and HPLC (BROWNKEE RP8 column) when eluted with 0.10 M HCl at a flow rate of 2 ml/min.

EXAMPLE 2

H—Glu—Glu—Ala—Glu—Asn—OH

The protected pentapeptide H—Glu(OBzl)—Glu(OBzl)—Ala—Glu(OBzl)—Asn—OBzl (100 mg, 0.1 mM) was dissovled in methanol (6 ml) containing acetic acid (2 drops) and hydrogenated in the presence of 10% Pd/C (200 mg) for 2.5 hrs. at 1 atm. and at room temperature. The catalyst was removed by filtration and the filtrate concentrated and lyophilized, yield; 48 mg (80%). Purification was accomplished by anion exchange chromatography (Bio-Rad AGI-X2).

Amino Acid Analysis:
Ala, 0.98; Asp, 1.04; Glu, 2.97.

The compound was adjudged to be homogeneous by TLC chromatography:

$R_f$ 0.19 (n-propanol:water; 7:3) and HPLC (BROWN-KEE RP8 column) when eluted with 0.01 M HCl at a flow rate of 2 ml/min.

EXAMPLE 3

Biological Activity

Cell Line

The AKR-derived, ouabain-resistant T lymphoma line BW 5147 was grown in Dulbecco's modified Eagle medium, supplemented with 50 units/ml penicillin, 50 μg/ml streptomycin, 2 mM glutamine, 1 mM sodium pyruvate and 10% fetal calf serum (medium I). At two-month intervals the line was grown in the presence of $10^{-3}$ M ouabain (strophanthin G, Calbiochem) for 5 days to eliminate any ouabain-sensitive foreign cells. Cells used in the present experiments were grown to high density (1.5–2×10$^6$/ml).

Incubation with Thymic Preparations and Assay For Specific Steroid Binding by Whole Cells Cell suspensions were centrifuged and washed 3 times with HBSS at 0°–4° (all centrifugations were carried out at 180×g for 5 min.). Incubation with thymosin $\alpha_1$, the carboxyl terminal octapeptide Glu—Val—Val—Glu—Glu—Ala—Glu—Asn, the carboxyl terminal pentapeptide Glu—Glu—Ala—Glu—Asn, and the carboxyl terminal tripeptide Ala—Glu—Asn of the present invention at different concentrations was carried out at 37° in a humidified atmosphere of 5% CO$_2$-95% air for various periods of time as indicated in the experimental data. The samples were prepared in petri dishes at 2.5–5×10$^6$ cells/ml in medium I. Duplicate samples were prepared for measuring total ($^3$H) dexamethasone[($^3$H) dex] binding and non-specific ($^3$H) dex binding by whole cells.

The assay for specific steroid binding by whole cells was modified from that of Sibley and Tomkins, Cell 2, 221 (1974). After incubation with thymic fractions duplicate cultures were harvested in polypropylene tubes and aliquots counted for viable cells by trypan blue exclusion in a hemacytometer. The cells were centrifuged and washed 3 times with 3 ml each of HBSS at 0°–4. The cells were resuspended in 1 ml of medium II (RPMI 1640 supplemented with 50 units/ml penicillin, 50 μg/ml streptomycin, 2 mM glutamine, 10 mM HEPES, pH 7.4) and 5×10$^{-9}$ M ($^3$H) dex was added to each of the duplicate cultures. One of these cultures also received a 1000 fold excess (5×10$^{-6}$M) of unlabeled dex (Sigma Chemical Co.) to determine specific ($^3$H) dex binding. This was taken as the difference in bound ($^3$H) dex between cells incubated in the absence (total) and presence (non-specific) of unlabeled dex. After incubation at 37° in a humidified atmosphere of 5% CO$_2$-95% air for 45–50 min, the cells were centrifuged, washed twice with 3 ml each of HBSS at 0°–4°, resuspended in 23° HBSS and left to stand at room temperature for 10 min before centrifugation. The samples were resuspended in 0.2 ml of Dulbecco's phosphate buffered saline (PBS) and transferred to scintillation vials with two 0.2 ml PBS washings. Biofluor (New England Nuclear) was added and the samples were counted for 10 min each in a Beckman LS-250 liquid scintillation counter. Typical standard deviation of the counts per min (CPM) was 0.7%.

Experiment 1

Incubation Period: 44 hrs

| Peptide | Dose (μg/ml) | ($^3$H) Dex Specifically Bound (CPM/2 × 10$^7$ cells) |
|---|---|---|
| None | — | 6,901 |
| Thymosin $\alpha_1$ | 1.0 | 7,703 |
| H—Glu—Glu—Ala—Glu—Asn—OH | 0.1 | 7,109 |
|  | 0.5 | 7,850 |
|  | 1.0 | 7,422 |
| H—Glu—Val—Val—Glu—Glu—Ala—Glu—Asn—OH | 0.1 | 7,467 |
|  | 0.5 | 7,858 |
|  | 1.0 | 7,835 |

Experiment 2

Incubation Period: 41 hr

| Peptide | Dose (μg/ml) | ($^3$H) Dex Specifically Bound (CPM/2 × 10$^7$ cells) |
|---|---|---|
| None | — | 10,352 |
| Thymosin Fraction 5 | 100 | 9,464 |
| H—Glu—Val—Val—Glu—Glu—Ala—Glu—Asn—OH | 0.5 | 9,103 |
|  | 1 | 9,804 |
| H—Glu—Glu—Ala—Glu—Asn—OH | 0.5 | 9,370 |
|  | 1 | 9,055 |
| Leu—Enkephalin | 0.5 | 10,005 |
|  | 1 | 10,056 |

Experiment 3

Incubation Period: 42 hr

| Peptide | Dose (μg/ml) | ($^3$H) Dex Specifically Bound (CPM/2 × 10$^7$ cells) |
|---|---|---|
| None | — | 9,865 |
| Thymosin $\alpha_1$ | 0.5 | 11,216 |
|  | 5 | 11,178 |
| H—Glu—Val—Val—Glu—Glu—Ala—Glu—Asn—OH | 0.5 | 11,614 |
| H—Glu—Glu—Ala—Glu—Asn—OH (repurified) | 0.5 | 9,219 |
|  | 5 | 7,866 |
| H—Ala—Glu—Asn—OH | 0.5 | 7,411 |
|  | 5 | 8,050 |
| H—Ala—Tyr—Met—Glu—OH | 0.5 | 10,020 |
|  | 5 | 9,725 |

Experiment 4

Incubation Period: 16 hr

| | | |
|---|---|---|
| None | — | 10,567 |
| None | — | 10,646 |
| Thymosin $\alpha_1$ | 0.1 | 9,002 |
|  | 0.5 | 9,383 |

-continued

|  | 5 | 9,051 |
| --- | --- | --- |
| H—Glu—Val—Val—Glu—Glu—Ala— | 0.01 | 9,093 |
| Glu—Asn—OH | 0.1 | 9,772 |
| H—Glu—Glu—Ala—Glu—Asn—OH | 0.5 | 9,812 |
| (repurified) |  |  |
| H—Ala—Glu—Asn—OH | 0.5 | 9,761 |
| H—Ala—Tyr—Met—Glu—OH | 0.01 | 9,988 |
|  | 0.1 | 10,566 |
|  | 0.5 | 10,888 |

It is thus seen that the tri- and pentapeptide compound of the present invention are active in converting precursor T cells into steroid sensitive $T_1$ cells or steroid resistant $T_2$ cells. Their activity is comparable to compounds and preparations having known T-cell maturation enhansing activity, such as thymosin fraction 5, thymosin $\alpha_1$, and the carboxyl terminal octapeptide of thymosin $\alpha_1$. On the other hand, peptides of the approximate same chain length and containing some of the same amino acids as the compounds of the invention were found to be devoid of activity, i.e., Leuenkephalin (H—Tyr—Gly—Gly—Phe—Leu—OH) and H—Ala—Tyr—Met—Glu—OH.

EXAMPLE 4

N-Benzyloxycarbonyl-γ-t-butyl-L-glutamyl-L-asparagine t-butyl ester

N-Benzyloxycarbonyl-γ-t-butyl-L-glutamate (50.7 g, 0.15 mol) in 300 ml freshly distilled THF was placed in a 2-liter 3-neck round bottom flask fitted with a thermometer, mechanical stirrer and dropping funnel and immersed in a dry ice-alcohol bath at −15°. N-Methylmorpholine (16.8 ml, 0.15 mol) was added dropwise. The temperature was maintained at −15° and isobutyl chloroformate (19.7 ml, 0.15 mol) was added dropwise over a 2-minute period. The reaction mixture was stirred an additional 2 minutes at −15° and a precooled solution of L-asparagine t-butyl ester (25.6 g, 0.136 mol) dissolved in 270 ml THF and 30 ml DMF was added dropwise over a 4-minute period while the temperature was maintained at −15°. The reaction mixture was stirred at −15° for 30 minutes and at 25° for 2.5 hours, evaporated in vacuo and the residue dissolved in EtOAc and washed with 10% NaHCO$_3$ (2×300 ml), saturated NaCl solution (30 ml), 1 M citric acid (2×300 ml) and saturated NaCl solution (300 ml). The organic layer was dried over MgSO$_4$, filtered and evaporated in vacuo to yield a thick oil. The oil was crystallized from EtOAc-ether to yield 34.5 g. Trituration of the mother liquid with ether gave an additional 31.1 g. Total yield 65.6 g (95%); mp 139° dec; R$_f$ 0.22 (CHCl$_3$:CH$_3$OH:AcOH:80-2-0.4). The analytical sample was prepared by recrystallization from methanol-ether; mp 142°–144.5°; $[\alpha]_D^{25}$ −19.14° (c 1, CH$_3$OH). Anal. calcd. for C$_{25}$H$_{37}$N$_3$O$_8$ (507.6): C, 59.16; H, 7.35; N, 8.28. Found: C, 59.24; H, 7.34; N, 8.40.

EXAMPLE 5

γ-t-Butyl-L-glutamyl-L-asparagine t-butyl ester

N-Benzyloxycarbonyl-γ-t-butyl-L-glutamyl-L-asparagine t-butyl ester (65.6 g, 0.13 mol) was dissolved in 580 ml CH$_3$OH, 5% Pd-BaSO$_4$ (15 g) added and hydrogenated in the Vibromixer apparatus for 3 hours. The reaction mixture was filtered through celite and evaporated in vacuo to yield a white foam 45.2 g (93%); R$_f$ 0.22 (CHCl$_3$:CH$_3$OH:85-10-5). The analytical sample was prepared by recrystallization from ethyl acetate-petroleum ether; mp 118°–120°; $[\alpha]_D^{25}$ −4.46° (c 1, CH$_3$OH). Anal. calcd. for C$_{17}$H$_{31}$N$_3$O$_6$ (373.5): C, 54.68; H, 8.37; N, 11.25. Found: C, 55.06; H, 8.76; N, 11.12.

EXAMPLE 6

N-Benzyloxycarbonyl-L-alanyl-γ-t-butyl-L-glutamyl-L-asparagine t-butyl ester

N-Benzyloxcarbonyl-L-alanine (31.93 g, 0.143 mol, 1.2 eq)was dissolved in THF (280 ml) and placed in a 2-liter 3-neck round bottom flask fitted with a thermometer, mechanical stirrer and immersed in a dry ice-alcohol bath at −20°. N-Methylmorphine (16.03 ml, 0.143 mol, 1.2 eq) was added with stirring via a dropping funnel over a 2- to 3-minute period. The temperature was maintained at −20° and isobutyl chloroformate (18.55 ml, 0.143 mol, 1.2 eq) was added over a 2-minute period. Stirring proceeded for 4 minutes at −15° and a precooled solution of H—Glu(OtBu)—Asn—OtBu (44.6 g, 0.119 mol) in THF (280 ml) was added portionwise over a 10-minute period while maintaining the temperature below −15°. Stirring proceeded at −15° for 30 minutes and at 25° for 3 hours. The reaction mixture was evaporated to dryness and the residue taken up in CHCl$_3$:10% NaHCO$_3$ (1.5 1:0.75 1) [some warming required]. The organic phase was washed with 10% NaHCO$_3$ (3×700 ml) and 10% NaCl (2×350 ml). The aqueous layers were back-extracted with CHCl$_3$ (3×300 ml) and the combined organic phase dried (MgSO$_4$), filtered and evaporated in vacuo to yield 85.2 g of crude product which crystallized from EtOAc. Yield: 56.40 g (81.7%); mp 164.5°–167°; R$_f$ 0.28 (CHCl$_3$:MeOH:AcOH; 80-20-5); $[\alpha]_D^{25}$ −34.44° (c 1, MeOH). Anal. calcd. for C$_{28}$H$_{42}$N$_4$O$_9$ (578.66): C, 58.12; H, 7.32; N, 9.68. Found: C, 57.81; H, 7.37; N, 9.44.

EXAMPLE 7

L-Alanyl-γ-t-butyl-L-glutamyl-L-asparagine t-butyl ester

N-Benzyloxycarbonyl-L-alanyl-γ-t-butyl-L-glutamyl-L-asparagine t-butyl ester (56.3 g, 0.0974 mol) was dissolved in CH$_3$OH (600 ml), 5% Pd-BaSO$_4$ (11 g) added and hydrogenated in the Vibromixer apparatus for 3 hours. The reaction mixture was filtered through celite, washed with ∼100 ml CH$_3$OH, and evaporated to an amber oil. The residue was crystallized from EtOAc-petroleum ether to yield 41.93 g (96.8%) of white crystalline product in 3 crops; mp 121°–123°; R$_f$ 0.18 (CHCl$_3$:MeOH:AcOH;80-20-5); $[\alpha]_D^{25}$ −20.32° (c 1, MeOH). Anal. calcd. for C$_{20}$H$_{36}$N$_4$O$_7$ (444.53): C, 54.04; H, 8.16; N, 12.60. Found: C, 54.27; H, 7.98; N, 12.52.

EXAMPLE 8

N-Benzyloxycarbonyl-γ-butyl-L-glutamyl-L-alanyl-γ-butyl-L-glutamyl-L-asparagine t-butyl ester N-Benzyloxycarbonyl-γ-t-butyl-L-glutamate DCHA (58.1 g, 0.112 mol, 1.2 eq) was dissolved in a mixture of EtOAc-0.5 N H$_2$SO$_4$ (375 ml each 1.66 eq). The organic phase was retained and extracted with 0.5 N H$_2$SO$_4$ (2×150 ml). The combined aqueous phase was back-extracted with EtOAc (2×150 ml), dried (MgSO$_4$), filtered and evaporated in vacuo to a yellow oil.

The residue, Z—Glu (OtBu)—OH (theory 37.3 g, 0.112 mol, 1.2 eq) was dissolved in THF (282 ml) and placed in a 2-liter, 3-neck round bottom flask fitted with a thermometer, mechanical stirrer and immersed in a dry ice-alcohol bath at −20°. N-Methylmorpholine (12.55 ml, 0.112 mol, 1.2 eq) was added dropwise. The temperature was maintained at −20° and isobutyl chloroformate (14.53 ml, 0.112 mol, 1.2 eq) was added dropwise over a 2-minute period. Stirring proceeded for a total of 4 minutes at −20° and a precooled solution of L-alanyl-γ-t-butyl-L-asparagine t-butyl ester (41.42 g, 0.0933 mol) in THF:DMF (293 ml:240 ml) was added portionwise over a 5-minute period while the temperature was maintained at −20°. Stirring continued at −15° for 30 minutes and at 25° for 16 hours.

The reaction mixture was evaporated in vacuo and the residue was taken up in $CHCl_3$:10% $NaHCO_3$ (1.2 l:0.6 l) [some warming required]. The organic layer was extracted with 10% $NaHCO_3$ (3×550 ml) and saturated NaCl (2×280 ml). The combined aqueous layer was back-extracted with $CHCl_3$ (3×240 ml). The combined organic layer was dried ($MgSO_4$), filtered and evaporated in vacuo to yield a white solid. Crystallization from EtOAc (475 ml): DMF (200 ml): petroleum ether (200 ml) gave 63.03 g (88.6%) of white crystalline product: mp 211°-212.5°: $R_f$ 0.89 ($CHCl_3$:MeOH:AcOH; 80-10-5: $[\alpha]_D^{25} -15.36°$ (c 1, DMF). Anal. calcd. $C_{37}H_{57}N_5O_{12}$ (763.89): C, 58.18; H, 7.52; N, 917. Found: C, 58.48; H, 7.56; N, 9.37.

EXAMPLE 9

γ-t-Butyl-L-glutamyl-L-alanyl-γ-t-butyl-L-glutamyl-L-asparagine t-butyl ester

Z—Glu(OtBu)—Ala—Glu(OtBu)—Asn—OtBu (63.03 g, 0.0814 mol) was dissolved in DMF (559 ml), 5% $Pd-BaSO_4$ (14.4 g) added and hydrogenated in the Vibromixer apparatus for 3 hours. The reaction mixture was filtered through celite, washed with ~100 ml DMF-MeOH, and evaporated in vacuo to an oil. The residue was crystallized from ether-petroleum ether to yield 48.46 g (94.4%) of white solid in 2 crops; mp 161°-164°; $R_f$ 0.70 (n-BuOH:AcOH:EtOAc:$H_2O$;1-1-1-1); $R_f$ 0.26 ($CHCl_3$:MeOH:AcOH;80-20-5); $[\alpha]_D^{25} -29.55°$ (c 1, MeOH). Anal. calcd. for $C_{29}H_{51}N_5O_{10}$ (629.75): C, 55.31; H, 8.16; N, 11.12. Found: C, 55.05; H, 7.80; N, 11.29.

EXAMPLE 10

L-Glutamyl-L-asparagine

γ-tert-Butyl-L-glutamyl-L-asparagine tert-butyl ester (0.50 g, 1.34 mmol) was placed in a 50 ml 1-neck round bottom flask, treated with a solution of TFA:$CH_2Cl_2$(5ml:5 ml) and stirred at 25° under $N_2$ for 2 hours. The reaction mixture was evaporated in vacuo and the residue was triturated with ether and dried in vacuo. This material was dissolved in 2% $NH_4OAc$ (pH 8.1) and applied onto a Bio-Rad AG1×2 column (1.5×20 cm)($OH^-$ form) which was equilibrated with 2% $NH_4OAc$ (pH 8.1). A gradient elution [0.02 M AcOH to 1.0 M AcOH] was utilized and fractions of 100 drops (5.7 ml) were collected and the product region was visualized by developing aliquots (10-20) of individual fractions on tlc. Fractions 11-23 (63-122 ml) were pooled and lyophilized to yield 254 mg (67.9%) of white solid; mp 189.5°-190.6°; $R_f$0.53 (n-BuOH:AcOH:EtOAc:$H_2O$; 1-1-1-1); $[\alpha]_D^{25} +7.25°$ (c 1, 0.1 M HCl). Anal. calcd. for $C_9H_{15}N_3O_6H_2O$ (279.3): C, 38.71; H, 6.14; N, 15.05. Found: C, 39.47; H, 5.88; N, 15.02.

EXAMPLE 11

L-Alanyl-L-glutamyl-L-asparagine

L-Alanyl-γ-t-butyl-L-glutamyl-L-asparagine t-butyl ester (500 mg, 1.13 mmol) was placed in a 50 ml 1-neck round bottom flask, treated with a solution of TFA:$CH_2Cl_2$ (5 ml:5 ml) and stirred at 25° under $N_2$ for 3 hours. The reaction mixture was evaporated in vacuo, triturated with ether, dried, taken up in 2% $NH_4OAc$ (pH 8.1) and applied onto a Bio-Rad AG1×2 column (1.5×20 cm) ($OH^-$ form) which was equilibrated with 2% $NH_4OAc$ (pH 8.1). A gradient elution [0.02 M AcOH to 1.0 M AcOH] was utilized and fractions of 100 drops (5.7 ml) were collected and the product region was visualized by developing aliquots (10λ to 20λ) of individual fractions on tlc. Fractions 9-16 (51-91 ml) were pooled and lyophilized to yield 226 mg (60.4%) of white solid; mp 178° dec; $R_f$ 0.47 (n-BuOH:AcOH-:EtOAc:$H_2O$; 1-1-1-1); $[\alpha]_D^{25} -20.47°$ (c 1.1, 0.1 M HCl). Anal. calcd. for $C_{12}H_{20}N_4O_7.1/2H_2O$ (341.3): C, 42.26; H, 6.20; N, 16.43. Found: C, 42.26; H, 6.17; N, 16.35.

EXAMPLE 12

L-Glutamyl-L-alanyl-L-glutamyl-L-asparagine

H—Glu(OtBu)—Ala—Glu(OtBu)—Asn—OtBu (500 mg, 0.794 mmol) was placed in a 50 ml 1-neck round-bottom flask, treated with a solution of TFA:$CH_2Cl_2$ (5 ml:5 ml) and stirred at 25° under $N_2$ for 3 hours. The reaction mixture was evaporated in vacuo, triturated with ether and dried to give 548 mg of crude product. A 297 mg portion was taken up in 2% $NH_4OAc$ (pH 8.1) was applied onto a Bio-Rad AG1×2 column (1.5×20 cm) ($OH^-$ form) which was equilibrated with 2% $NH_4OAc$ (pH 8.1). A gradient elution [0.02 M AcOH to 1.0 M AcOH] was utilized and fractions of 100 drops (5.7 ml) were collected and the product region was visualized by developing aliquots (10λ-20λ) of individual fractions on tlc. Fractions 24-38 (137-217 ml) were pooled and lyophilized to yield 159 mg (80.3%) of white solid; mp 211.5°-214.5° dec; $R_f$ 0.47 (n-BuOH-:AcOH:EtOAc:$H_2O$; 1-1-1-1-); $[\alpha]_D^{25} -37.25°$ (c 1, 0.1 M HCl). Anal. calcd. for $C_{17}H_{28}N_5O_{10}$(462.4): C, 44.15; H, 6.10; N, 15.14. Found: C, 43.91; H, 6.42; N, 14.83.

EXAMPLE 13

N-Benzyloxycarbonyl-L-valyl-γ-t-butyl-L-glutamic acid methyl ester

N-Benzyloxycarbonyl-L-valine (52.4 g, 0.21 mol) was dissolved in 400 ml freshly distilled THF and stirred mechanically in a 2-liter 3-neck round bottom flask fitted with a thermometer and dropping funnel and immersed in a dry ice-alcohol bath at −15°. While stirring at −15°, N-methylmorpholine (23 ml, 0.21 mol) was added dropwise. The temperature was maintained at −15° and isobutyl chloroformate (27.6 ml, 0.21 mol) was added dropwise over a 2-minute period. The reaction mixture stirred for an additional 2 minutes at −15° and a precooled (−20° ) solution of L-glutamic acid α-methyl ester γ-t-butyl ester (60.4 g, 0.21 mol) dissolved in 300 ml THF and 80 ml DMF was added dropwise with simultaneous addition of N-methylmorpholine (23.5 ml, 0.21 mol). The addition took 5 minutes while maintaining the temperature below −15°. The reaction mixture was stirred for 30 minutes at −15°, and for 2.5 hours at 25°, evaporated in vacuo and the residue dissolved in EtOAc (600 ml) and washed with 10% NaHCO$_3$ (3×100 ml), 1 M citric acid (3×100 ml) and saturated NaCl solution (1×100 ml). The aqueous washes were back-washed with EtOAc and the combined layers were dried over MgSO$_4$, filtered and concentrated to ~100 ml and pet. ether added. The solid was collected and dried in vacuo to yield 73.9 g (78%). Recrystallization from CCl$_4$/pet.ether gave 66.7 g of white crystalline product; mp 66.5°–68°; R$_f$ 0.74 (n-BuOH:AcOH:EtOAc:H$_2$O; 1-1-1-1-); [α]$_D^{25}$ −28.91°, (c 1, MeOH). Anal. calcd. for C$_{23}$H$_{34}$N$_2$O$_7$ (450.5): C, 61.32; H, 7.61; N, 6.22. Found: C, 61.23; H, 7.58; N, 6.01.

EXAMPLE 14

N-Benzyloxycarbonyl-L-valyl-γ-t-butyl-L-glutamic acid α-hydrazide

Z—Val—Glu(OtBu)—OMe (0.50 g, 1-1 mmol) was dissolved in DMF (10 ml) and n-BuOH (10 ml) and placed i a 50 ml round bottom flask. The H$_2$NNH$_2$.H$_2$O (5.3 ml, 0.11 mol, 100 eq) was added and the reaction mixture stirred magnetically at 25° for 17 hours. The reaction mixture was evaporated in vacuo and the residue recrystallized from i-PrOH. Several crops of product were collected to yield 0.256 g (51%), mp, 143°–145°; R$_f$ 0.83 (n-BuOH:AcOH:EtOAc:H$_2$O:1-1-1-1); R$_f$ 0.64 (CHCl$_3$:CH$_3$OH:AcOH:80-5-1); [α]$_D^{25}$ −33.09° (c 1, MeOH). Anal. calcd. for C$_{22}$H$_{34}$N$_4$O$_6$ (450.54): C, 58.65; H, 7.61; N, 12.44. Found: C, 58.17; H, 7.60; N, 12.45.

EXAMPLE 15

γ-t-Butyl-L-glutamyl-L-alanyl-γ-t-butyl-L-glutamyl-L-asparagine t-butyl ester

Z—Glu(OtBu)—Ala—Glu(OtBu)—Asn—OtBu (63.03 g, 0.0814 mol) was dissolved in DMF (559 ml), 5% Pd-BaSO$_4$ (14.4 g) added and hydrogenated in the Vibromixer apparatus for 3 hours. The reaction mixture was filtered through celite, washed with ~100 ml DMF-MeOH, and evaporated in vacuo to an oil. The residue was crystallized from ether-petroleum ether to yield 48.46 g (94.4%) of white solid in 2 crops; mp 161°–164°; R$_f$ 0.70 (n-BuOH:AcOH:EtOAc:H$_2$O; 1-1-1-1); R$_f$ 0.26 (CHCl$_3$:MeOH:AcOH:80-20-5); [α]$_D^{25}$ −29.55° (c 1, MeOH). Anal. calcd. for C$_{29}$H$_{51}$N$_5$O$_{10}$ (629.75): C, 55.31; H, 8.16; N, 11.12. Found: C, 55.05; H, 7.80; N, 11.29.

EXAMPLE 16

N-Benzyloxycarbonyl-L-valyl-γ-t-butyl-L-glutamyl-γ-t-butyl-L-glutamyl-L-alanyl-γ-t-butyl-L-glutamyl-L-asparagine t-butyl ester Z—Val—Glu(OtBu)—NHNH$_2$ (0.441 g, 0.98 mmol) was dissolved in DMF (12 ml) and placed in a 50 ml 3-neck round bottom flask fitted with a thermometer, dropping funnel and drying tube and immersed in a dry ice-alcohol bath at −20°. The solution was treated with 3.1 N HCl-THF (1.9 ml, 5.88 mmol, 6 eq) and isamylnitrite (0.196 ml, 1.46 mmol, 1.5 eq.) and stirred at −20° for 30 minutes. The temperature was lowered to −25° and Et$_3$N (0.82 ml, 5.88 mmol, 6 eq) added. The temperature was readjusted to −20° and a solution of H—Glu(OtBu)—Ala—Glu(OtBu)—Asn—OtBu (0.679 g, 1.08 mmol, 1.1 eq) in DMF (6 ml) was added followed by the addition of Et$_3$N (0.16 ml). The pH was maintained at 8.0 by periodic addition of Et$_3$N. The reaction mixture was stirred 30 minutes at −20°, 16 hours at 7° and 5 hours at 25°, evaporated in vacuo and the residue triturated with warm THF. The remaining solid was washed with H$_2$O (4×30 ml) and the residual solid combined with the product remaining after evaporation of the THF wash. Recrystallization from CH$_3$OH gave 0.469 g (45.5%); mp 217°–219°; R$_f$ 0.45 (CHCl$_3$:CH$_3$OH:AcOH:80-5-1); [α]$_D^{25}$ −16.19° (c 1, DMSO). Anal. calcd. for C$_{51}$H$_{81}$N$_7$O$_{16}$ (1048.18): C, 58.44; H, 7.79; N, 9.35. Found: C, 58.19; H, 7.71; N, 9.41.

EXAMPLE 17

L-Valyl-γ-t-butyl-L-glutamyl-γ-t-butyl-L-glutamyl-L-alanyl-γ-t-butyl-L-glutamyl-L-asparagine t-butyl ester Z—Val—Glu(OtBu)—Glu(OtBu)—Ala—Glu(OtBu)—Asn—OtBu (0.418 g, 0.4 mmol) was dissolved in DMF (30 ml), 5% Pd-BaSO$_4$ (0.4 g) added and hydrogenated in the vibromixer apparatus for 3 hours. The reaction mixture was filtered through celite, washed with DMF (~30 ml) and evaporated in vaco to yield a white foam which was recrystallized from i-PrOH-petroleum ether to afford 0.351 g (96%) of white solid; mp 227° dec.; R$_f$ 0.71 (n-BuOH:EtOAc:H$_2$O:AcOH;1-1-1-1); [α]$_D^{25}$ −18.86° (c 1, DMSO). Anal. calcd. for C$_{43}$H$_{75}$N$_7$O$_{14}$.H$_2$O (914.11): C, 55.41; H, 8.33; N, 10.52. Found: C, 55.38; H, 8.06; N,10.55.

EXAMPLE 18

L-Valyl-L-glutamyl-L-glutamyl-L-alanyl-L-glutamyl-L-asparagine

H—Val—Glu(OtBu)—Glu(OtBu)—Ala—Glu(OtBu)—Asn—OtBu (0.310 g, 0.33 mmol) was placed in a 15 ml round bottom flask, treated with a solution of TFA:CH$_2$Cl$_2$ (2.5 ml:2.5 ml) and stirred at 25° under N$_2$ for 3 hours. The reaction mixture was evaporated in vacuo and the residue applied onto a Dowex 1×2 column (1.5×20 cm) in a minimum amount of 2% NH$_4$OAc (pH 8.1). [The column (OH$^-$ form) had been equilibrated with 2% NH$_4$OAc, pH 8.1]. A gradient elution (0.01 M AcOH to 0.1 M AcOH) was used and fractions of 100 drops (5.7 ml) were collected. The product fractions were visualized by developing aliquots of individual fractions on tlc (fluorescamine spray procedure). Fractions 56-67 (319–282 ml) were combined and lyophilized to yield 0.134 g (59%) of white solid; mp 244°–245° dec.; R$_f$ 0.50 (n-BuOH:EtOAc:H$_2$O:AcOH;1-1-1-1); R$_f$ 0.29 (n-BuOH:AcOH:Pyr:H$_2$O;15-3-10-12); [α]$_D^{25}$ −67.77° (c 0.8, 0.1 M HCl). Amino acid anal. (6 M HCl, 110°, 24 hours): Asp, 1.02; Glu, 2.88; Ala, 1.01; Val, 1.08. Anal. calcd. for C$_{27}$H$_{43}$N$_7$O$_{14}$.H$_2$O (707.7): C, 45.82; H, 6.41; N, 13.85. Found: C, 46.14; H, 6.25; N, 13.82.

EXAMPLE 19

N-Benzyloxycarbonyl-L-valyl-L-valyl-γ-t-butyl-L-glutamic acid α-methyl ester

N-Benzyloxycarbonyl-L-valyl-γ-t-butyl-L-glutamic acid methyl ester (33.9 g, 75.3 mmol) was dissolved in DMF:THF (40 ml:150 ml), 5% Pd-BaSO$_4$ (7.5 g) added and hydrogenated in the Vibromixer apparatus for 2.5 hours. The reaction mixture was filtered through celite, cooled to 0° and the resultant solution of L-valyl-γ-t-butyl-L-glutamic acid methyl ester was placed in the freezer until use in the coupling stage below.

N-Benzyloxycarbonyl-L-valine (22.7 g, 90.4 mmol) was dissolved in 20 ml freshly disilled THF in a 1-liter 3-neck round bottom flask fitted with a thermometer, mechanical stirrer and dropping funnel and immersed in a dry ice-alcohol bath at −15°. While stirring at −15°, N-methylmorpholine (10.1 ml, 90.4 mmol) was added. This was followed by the addition of isobutyl chloroformate (11.9 ml, 90.4 mmol) dropwise over a 2-minute period. The reaction was stirred an additional 2 minutes at 31 15° and the precooled (−20°) solution of L-valyl-γ-t-butyl-L-glutamic acid α-methyl ester (75.3 mmol from above) was added over a 4.5 minute period. The reaction mixture was stirred at −15° for 30 minutes and at 25° for 17 hours, evaporated in vacuo and the residue dissolved in CHCl$_3$ and washed with 10% NaHCO$_3$ (4×250 ml), saturated NaCl (1×200 ml), 1 M citric acid (2×200 ml) and saturated NaCl (1×200 ml). The aqueous phases were back-washed with CHCl$_3$ and the combined organic layers dried over MgSO$_4$, filtered and evaporated in vacuo. The product was recrystallized from 1-PrOH to yield 25.4 g (62%) of white crystalline product; mp 204°-204°; R$_f$ 0.47 (CHCl$_3$:CH$_3$OH:AcOH;80-2-0.4); [α]$_D^{25}$−7.40° (c 1, DMF). Anal. calcd. for C$_{28}$H$_{43}$N$_3$O$_8$ (549.7): C, 61.18; H, 7.89; N, 7.64. Found: C, 61.43; H, 7.96; N, 7.41.

EXAMPLE 20

N-Benzyloxycarbonyl-L-valyl-L-valyl-γ-t-butyl-L-glutamic acid hydrazide

Z—Val—Val—Glu(OtBu)—OMe (0.50 g, 0.91 mmol) was dissolved in DMF (10 ml) and n-BuOH (10 ml), stirred magnetically at 25° and hydrazine hydrate (4.3 ml, 0.09 mol, 100 eq) added. The reaction mixture was stirred for 17 hours and evaporated in vacuo. The residue was dissolved in warm CH$_3$OH (∼10 ml), water added and the precipitated product collected and dried to yield 0.456 g (91%) of white solid; mp 221° dec.; R$_f$ 0.38 (CHCl$_3$:CH$_3$OH:AcOH;80-5-1); [α]$_D^{25}$−0.56° (c 1, DMSO). Anal. calcd. for C$_{27}$H$_{43}$N$_5$O$_7$.H$_2$O (567.67): C, 57.13; H, 7.99; N, 12.34. Found: C, 57.15; H, 7.69; N, 12.87.

EXAMPLE 21

N-Benzyloxycarbonyl-L-valyl-L-valyl-γ-t-butyl-L-glutamyl-γ-t-butyl-L-glutamyl-L-alanyl-γ-t-butyl-L-glutamyl-L-asparagine t-butyl ester A suspension of Z—Val—Val—Glu(OtBu)—NHNH$_2$ (0.275 g, 0.5 mmol) in DMF (6 ml) was placed in a 50 ml 3-neck round bottom flask fitted with a thermometer and drying tube and immersed in a dry ice-alcohol bath at −20°. The mixture was treated with 2.9 N HCl-THF (1.0 ml, 3 mmol, 6 eq). Isoamylnitrite (0.10 ml, 0.72 mmol, 1.45 eq) was added and stirring continued for 30 minutes at −20°. The reaction mixture was cooled at −25° and Et$_3$N (0.42 ml, 3 mmol, 6 eq) was added. The temperature was readjusted to −20° and a solution of H—Glu(OtBu)—Ala—Glu(OtBu)—Asn—OtBu (0.346 mg, 0.55 mmol, 1.1 eq) in DMF (3 ml) was added followed by the addition of Et$_3$N (0.08 ml, 0.55 mmol, 1.1 eq). The pH was maintained at 8.0 by periodic addition of Et$_3$N. Stirring proceeded for 30 minutes at −20°, 16 hours at 7° and 5 hours at 25°. The reaction mixture was evaporated in vacuo and the residue triturated with H$_2$O. The residual solid was dried in vacuo to yield 0.495 g (85%). The product was recrystallized from CH$_3$OH-H$_2$O to give 0.423 g (73.7%); mp 230.5°-231.5° dec.; R$_f$ 0.88 (n-BuOH:EtOAc:H$_2$O:AcOH,1-1-1-1); [α]$_D^{25}$−19.20° (c 1, DMSO). Anal. calcd. for C$_{56}$H$_{90}$N$_8$O$_{17}$ (1147.34) C, 58.62; H, 7.91; N, 9.77. Found: C, 58.49; H, 7.78; N, 9.90.

EXAMPLE 22

L-Valyl-L-valyl-γ-t-butyl-L-glutamyl-γ-t-butyl-L-glutamyl-L-alanyl-γ-t-butyl-L-glutamyl-L-asparagine t-butyl ester Z—Val—Val—Glu(OtBu)—Glu(OtBu)—Ala—Glu(OtBu)—Asn—OtBu (0.308 g, 0.27 mmol) was dissolved in DMF (35 ml), 10% Pd-C (0.36 g) added and hydrogenated in the Vibromixer apparatus for 2 hours. The reaction mixture was filtered through celite and evaporated in vacuo. The residue was dissolved in i-PrOH, H$_2$O added and the white solid collected and dried to yield 0.231 g (84.3%); mp 229°-231°; R$_f$ 0.74 (n-BuOH:EtOAc:H$_2$O:AcOH; 1-1-1-1); R$_f$ 0.53 (n-BuOH:AcOH:H$_2$O; 4-1-1). Anal. calcd. for C$_{48}$H$_{84}$N$_8$O$_{15}$ (1013.24): C, 56.90; H, 8.36; N, 11.06. Found: C, 57.16, H, 8.13, N, 10.83.

EXAMPLE 23

L-Valyl-L-valyl-L-glutamyl-L-glutamyl-L-alanyl-L-glutamyl-L-asparagine

H—Val—Val—Glu(OtBu)—Glu(OtBu)—Ala—Glu(OtBu)—Asn—OtBu (146 mg, 0.144 mmol) was placed in a 10 ml 1-neck round bottom flask, treated with a solution of TFA:CH$_2$Cl$_2$ (2.5 ml: 2.5 ml) and stirred at 25° under N$_2$ for 3 hours. The reaction mixture was evaporated in vacuo, taken up in 2% NH$_4$OAc (pH 8.1) and applied onto a Bio-Rad AG1×2 column (1.5×20 cm) (OH$^-$ form) which was equilibrated with 2% NH$_4$OAc (pH 8.1). A gradient elution [0.02 M AcOH to 1.0 M AcOH] was utilized and fractions of 50 drops (2.8 ml) were collected and the product region was visualized by developing aliquots (10λ–20λ) of individual fractions on tlc. Fractions 88–89 (246–277 ml) were pooled and lyophilized to yield 48 mg (40.3%) of white solid; mp 235°-238° dec.; R$_f$ 0.58 (n-BuOH:AcOH:EtOAc:H$_2$O, 1-1-1-1); R$_f$ 0.22 (n-BuOH:AcOH:Pyr:H$_2$O; 15-3-10-12); [α]$_D^{25}$−75.59° (c 0.8, 0.1 M HCl). Anal. calcd. for C$_{32}$H$_{52}$N$_8$O$_{15}$.2H$_2$O (824.85): C, 46.60, H, 6.85; N, 13.58. Found: C, 46.96; H, 6.59; N, 13.26.

EXAMPLE 24

Most thymic lymphocytes reside in the cortex (90-95%) and are characterized by high levels of surface Thy-1 and TL, low levels of H-2 antigen, immunoincompetence and glucocorticoid sensitivity. The thymus medulla contains about 3-5% of all thymocytes characterized by low Thy-1, TL$^-$, high H-2,glucocorticoid resistance and immunocompetence. It has been shown that at least part of these medullary cells are derived from glucocorticoid—sensitive cortical precursors. It is also widely held that these medullary cells are the source of peripheral T lymphocytes; although this is still controversial. Experiments have shown that when mouse thymocytes were treated for approximately 16 hours with thymosin F-5 or α$_1$ and then exposed to glucocorticoids, the percentage of cells resistant to the steroids was higher than untreated cells. Cells treated with mouse splenic F-3, on the other hand, showed no changes in steroid sensitivity.

In the experiment described in Table 1, mouse thymus cells previously treated with thymosin fraction 5 (F-5) or thymosin alpha 1 (α$_1$) were subsequently exposed to glucocorticoids (hydrocortisone (HC) or dexamethasone (dex). A higher percentage of thymosin-treated cels survived the killing effect of glucocorticoids as compared to untreated cells. Optimum concentrations of thymosin for the response appeared to be 100 μg F-5 and 1 μg $\alpha_1$ per mL of culture medium. Mouse splenic fraction 3 (F-3) at up to 200 μg protein per mL medium did not show any effect. Table 2 shows the actual number of viable cells following various treatments in 3 typical experiments in which the period of exposure of HC was varied from 4 to 9.5 hrs. In each case treatment with Thymosin F-5 or $\alpha_1$ increased the percentage of cells surviving the HC exposure over untreated cells. Table 3 contains the results obtained with the C-terminal fragments of Thymosin $\alpha_1$ in comparison with Thymosin Fraction 5 and/or Thymosin $\alpha_1$ and shows that the fragments of the present invention also increased the percentage of surviving cells. H—Glu—Val—Val—Glu—OH is the N-terminal half of the Octapeptide C-8 and did not exhibit a dosage response. (It is noted that incubation with Thymosin F-5 or mouse splenic F-3 invariably decreased cell death in non-HC-treated HC⁻) cultures. After a typical 21-hour total incubation period, an average of 34% of the control cells were viable while an average of 48% of the thymosin-treated C⁻ cells survived. Viable cells in Thymosin $\alpha_1$-treated HC⁻ cultures were comparable to control HC⁻ cultures).

In these tables the designation C-2 through C-8 are intended to mean the following compounds:

$C_2$ = H—Glu—Asn—OH
$C_3$ = H—Ala—Glu—Asn—OH
$C_4$ = H—Glu—Ala—Glu—Asn—OH
$C_5$ = H—Glu—Glu—Ala—Glu—Asn—OH
$C_6$ = H—Val—glu—Glu—Ala—Glu—Asn—OH
$C_7$ = H—Val—Val—Glu—Glu—Ala—Glu—Asn—OH
$C_8$ = H—Glu—Val—Val—Glu—Glu—Ala—Glu—Asn—OH

TABLE 1

Effect of Thymosin F-5 and $\alpha_1$ on Glucocorticoid Resistance of Mouse Thymus Cells under Serum-Free Conditions.

| Treatment | Concentration (μg/ml) | % Cell Survival |
|---|---|---|
| None | — | 68.2 ± 2.2 |
| Thymosin F-5 | 50 | 83.2 ± 4.8 |
| | 100 | 91.5 ± 2.0 |
| | 150 | 88.9 ± 2.6 |
| | 200 | 88.0 ± 2.9 |
| Thymosin $\alpha_1$ | 0.1 | 84.0 ± 1.3 |
| | 1.0 | 95.0 ± 0.9 |
| Mouse Splenic F-3 | 100 | 60.0 ± 5.1 |
| | 200 | 69.4 ± 0.7 |

Mouse thymus cells were incubated at 37° for 16 hours in the absence and presence of thymosin followed by an additional 5-hour incubation (37°) with and without $10^{-5}$ M HC or dex. The number of cells excluding trypan blue was determined at the end of the total incubation period by Cytograf cell counter analysis. Percent cell survival was expressed as

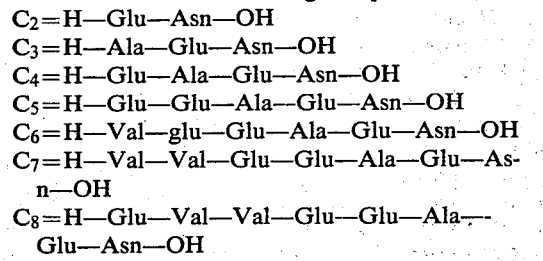

Values shown are the mean ±S.E. of 2-4 separate experiments.

TABLE 2

Effect of Thymosin on Mouse Thymus Cell Survival Following Various Periods of Exposure to Glucocorticoids under Serum-Free Conditions.

| Treatment | Concentration (μg/ml) | No. Viable Cells/ml ($\times 10^{-6}$) +HC | No. Viable Cells/ml ($\times 10^{-6}$) −HC | Cell Survival (%) |
|---|---|---|---|---|
| Experiment No. 1 | | | | |
| None | — | 2.63 | 3.86 | 68.1 |
| Thymosin F-5 | 25 | 3.35 | 4.23 | 79.2 |
| | 50 | 3.31 | 4.12 | 80.3 |
| | 100 | 4.05 | 4.48 | 90.4 |
| | 150 | 3.97 | 4.63 | 85.7 |
| | 200 | 3.96 | 4.80 | 82.5 |
| Thymosin $\alpha_1$ | 0.1 | 3.30 | 3.87 | 85.3 |
| | 1.0 | 3.29 | 3.63 | 90.6 |
| Mouse Splenic F-3 | 100 | 3.21 | 4.80 | 65.0 |
| | 200 | 3.28 | 4.77 | 68.8 |
| Experiment No. 2a | | | | |
| None | — | 2.92 | 3.73 | 78.3 |
| Thymosin F-5 | 25 | 3.24 | 3.94 | 82.2 |
| | 50 | 3.45 | 3.80 | 90.8 |
| | 100 | 3.66 | 3.80 | 96.3 |
| | 150 | 4.08 | 4.50 | 90.7 |
| | 200 | 3.93 | 4.24 | 92.7 |
| Thymosin $\alpha_1$ | 0.1 | 2.93 | 3.34 | 87.7 |
| | 0.5 | 3.01 | 3.34 | 90.0 |
| | 1.0 | 3.48 | 3.50 | 99.4 |
| Experiment 2b* | | | | |
| None | — | 1.26 | 2.89 | 43.6 |
| Thymosin F-5 | 25 | 1.65 | 3.23 | 51.1 |
| | 50 | 1.94 | 3.31 | 58.6 |
| | 100 | 1.95 | 3.46 | 56.4 |
| | 150 | 2.19 | 3.42 | 64.0 |
| | 200 | 2.42 | 3.80 | 63.7 |
| Thymosin $\alpha_1$ | 0.1 | 1.58 | 2.36 | 66.9 |
| | 1.0 | 1.44 | 2.59 | 55.6 |

See Table 1 for experimental details.
*Incubation period in the presence and absence of HC:
Experiment No. 1-5 hours.
Experiment No. 2a-4 hours.
Experiment No. 2b-9.5 hours.

TABLE 3

Effect of Thymosin F-5, $\alpha_1$, and C-terminal Fragments on Glucocorticoid Resistance of Mouse Thymus Cells under Serum-Free Conditions.

| Treatment | Concentration (μg/ml) | No. Viable Cells/ml ($\times 10^{-6}$) +HC | No. Viable Cells/ml ($\times 10^{-6}$) −HC | Cell Survival (%) |
|---|---|---|---|---|
| Experiment No. 1 | | | | |
| None | — | 2.71 | 3.77 | 71.9 |
| Thymosin F-5 | 50 | 3.31 | 4.12 | 80.4 |
| | 100 | 4.05 | 4.48 | 90.3 |
| | 150 | 3.97 | 4.63 | 85.8 |
| | 200 | 3.96 | 4.80 | 82.4 |
| Thymosin $\alpha_1$ | 0.1 | 3.30 | 3.87 | 85.2 |
| | 1.0 | 3.29 | 3.63 | 90.7 |
| C-8 | 0.1 | 2.90 | 3.30 | 87.9 |
| | 1.0 | 3.11 | 3.37 | 92.1 |
| C-7 | 0.1 | 2.95 | 3.72 | 79.3 |
| | 1.0 | 3.07 | 3.63 | 84.7 |
| C-6 | 0.1 | 3.13 | 3.41 | 98.3 |
| | 1.0 | 2.97 | 3.13 | 94.7 |
| H—Ala—Tyr—Met—Glu—OH | 0.1 | 2.71 | 3.42 | 79.3 |
| | 1.0 | 2.78 | 3.72 | 74.8 |

| Treatment | Concentration (μg/ml) | No. Viable Cells/ml ($\times 10^{-6}$) +HC | No. Viable Cells/ml ($\times 10^{-6}$) −HC | Cell Survival (%) |
|---|---|---|---|---|
| Experiment No. 2 | | | | |
| None | — | 2.30 | 3.32 | 69.4 |

-continued

| Treatment | Concentration (µg/ml) | No. Viable Cells/ml (× 10⁻⁶) +HC | −HC | Cell Survival (%) |
|---|---|---|---|---|
| Thymosin α$_1$ | 0.1 | 2.29 | 2.77 | 82.7 |
| | 1.0 | 3.16 | 3.18 | 99.2 |
| C-8 | 0.1 | 2.65 | 3.08 | 85.9 |
| | 1.0 | 2.98 | 3.12 | 95.5 |
| C-7 | 0.1 | 2.15 | 2.93 | 73.5 |
| | 1.0 | 2.77 | 3.46 | 80.1 |
| C-6 | 0.1 | 2.77 | 3.29 | 84.3 |
| | 1.0 | 2.76 | 3.32 | 83.1 |
| C-5 | 0.1 | 2.29 | 3.09 | 74.1 |
| | 1.0 | 2.92 | 3.41 | 85.5 |
| C-4 | 0.1 | 2.43 | 3.12 | 78.0 |
| | 0.5 | 2.72 | 3.41 | 79.6 |
| C-3 | 0.1 | 2.52 | 3.79 | 66.5 |
| | 0.5 | 2.76 | 3.58 | 77.0 |
| C-2 | 0.1 | 2.60 | 3.63 | 71.6 |
| | 0.5 | 2.66 | 3.42 | 77.7 |
| H—Glu—Val—Val—Glu—OH | 0.1 | 2.41 | 3.27 | 73.7 |
| | 0.5 | 2.48 | 3.36 | 73.9 |

I claim:

1. A compound of the formula

X—Glu—Asn—OH where
X is H, H—Ala—, H—Glu—Glu—Ala—, H—Val—Glu—Glu—Ala— and H—Val—Val—Glu—Glu—Ala—
and the pharamaceutically acceptable salts thereof.

2. The compound of claim 1 which is H—Glu—Asn—OH.

3. The compound of claim 1 which is H—Ala—Glu—Asn—OH.

4. The compound of claim 1 which is H—Glu—Glu—Ala—Glu—Asn—OH.

5. The compound of claim 1 which is H—Val—Glu—Glu—Ala—Glu—Asn—OH.

6. The compound of claim 1 which is H—Val—Val—Glu—Glu—Ala—Glu—Asn—OH.

* * * * *